US012734270B2

(12) United States Patent
Bucevschi et al.

(10) Patent No.: US 12,734,270 B2
(45) **Date of Patent: *Sep. 15, 2026**

(54) PROCESS FOR THE PRODUCTION OF BIODEGRADABLE SUPERABSORBENT POLYMER WITH HIGH ABSORBENCY UNDER LOAD BASED ON STYRENE MALEIC ACID COPOLYMERS AND BIOPOLYMER

(71) Applicant: POLYGREEN LTD, Tel Aviv (IL)

(72) Inventors: Mircea Dan Bucevschi, Rehovot (IL); Zvi Meiri, Netanya (IL); Shai Shahal, Tel Aviv (IL)

(73) Assignee: POLYGREEN LTD, Tel Aviv (IL)

( * ) Notice: Subject to any disclaimer, the term of this patent is extended or adjusted under 35 U.S.C. 154(b) by 100 days.

This patent is subject to a terminal disclaimer.

(21) Appl. No.: 18/907,923

(22) Filed: Oct. 7, 2024

(65) Prior Publication Data

US 2025/0025597 A1 Jan. 23, 2025

Related U.S. Application Data

(63) Continuation of application No. 17/044,728, filed as application No. PCT/US2019/025362 on Apr. 2, 2019, now Pat. No. 12,128,144.

(60) Provisional application No. 62/651,423, filed on Apr. 2, 2018.

(51) Int. Cl.

| | |
|---|---|
| ***A61L 15/60*** | (2006.01) |
| ***A61L 15/22*** | (2006.01) |
| ***A61L 15/32*** | (2006.01) |
| ***A61L 15/62*** | (2006.01) |
| ***C08F 8/12*** | (2006.01) |
| ***C08F 22/06*** | (2006.01) |
| ***C08L 25/08*** | (2006.01) |
| ***C08L 35/06*** | (2006.01) |

(52) U.S. Cl.
CPC ............. *A61L 15/60* (2013.01); *A61L 15/225* (2013.01); *A61L 15/325* (2013.01); *A61L 15/62* (2013.01); *C08F 8/12* (2013.01); *C08F 22/06* (2013.01); *C08L 25/08* (2013.01); *C08L 35/06* (2013.01); *C08L 2201/06* (2013.01)

(58) Field of Classification Search
CPC .......... C08L 35/06; C08L 35/08; C08L 33/02; A61L 15/60
See application file for complete search history.

(56) References Cited

U.S. PATENT DOCUMENTS

| | | | |
|---|---|---|---|
| 2,479,522 | A | 8/1949 | Strain |
| 2,640,819 | A | 6/1953 | Barrett |
| 2,855,387 | A | 10/1958 | Barrett |
| 2,996,480 | A | 8/1961 | Mulloy et al. |
| 3,933,747 | A | 1/1976 | Nowak et al. |
| 3,948,866 | A | 4/1976 | Pennewiss et al. |
| 3,954,721 | A | 5/1976 | Gross |
| 3,959,569 | A | 5/1976 | Burkholder, Jr. |
| 3,966,902 | A | 6/1976 | Chromecek |
| 3,980,663 | A | 9/1976 | Gross |
| 3,983,095 | A | 9/1976 | Bashaw et al. |
| 3,983,271 | A | 9/1976 | Pangle, Jr. et al. |
| 3,989,586 | A | 11/1976 | Bashaw et al. |
| 3,993,553 | A | 11/1976 | Assarsson et al. |
| 3,997,484 | A | 12/1976 | Weaver et al. |
| 4,034,014 | A | 7/1977 | Curtis, Jr. et al. |
| 4,036,788 | A | 7/1977 | Steckler |
| 4,041,228 | A | 8/1977 | Gross |
| 4,051,311 | A | 9/1977 | Lee |
| 4,058,124 | A | 11/1977 | Yen et al. |
| 4,076,673 | A | 2/1978 | Burkholder, Jr. |
| 4,076,917 | A | 2/1978 | Swift et al. |
| 4,101,606 | A | 7/1978 | Cenci et al. |
| 4,116,899 | A | 9/1978 | Fanta et al. |
| 4,117,184 | A | 9/1978 | Erickson et al. |
| 4,154,646 | A | 5/1979 | Rave |
| 4,163,092 | A | 7/1979 | Steckler |
| 4,167,464 | A | 9/1979 | George |
| 4,238,374 | A | 12/1980 | Durham et al. |
| 4,241,537 | A | 12/1980 | Wood |
| 4,251,643 | A | 2/1981 | Harada et al. |
| 4,340,706 | A | 7/1982 | Obayashi et al. |
| 4,389,513 | A | 6/1983 | Miyazaki |
| 4,390,672 | A | 6/1983 | von Bonin |

(Continued)

FOREIGN PATENT DOCUMENTS

| | | | |
|---|---|---|---|
| CN | 106146156 | A | 11/2016 |
| CN | 106348949 | A | 1/2017 |

(Continued)

OTHER PUBLICATIONS

Enas M. Ahmed Hydrogel: Preparation, characterization and applications: A review, Journal of Advanced Research vol. 6, Issue 2, Mar. 2015, pp. 105-121.
Fidelia Nnadi and Chris Brave "Environmentally friendly superabsorbent polymers for water conservation in agricultural lands"—Journal of Soil Science and Environmental Management vol. 2(7), pp. 206-211, Jul. 2011.
Giuseppe Cannazza, Andrea Cataldo, Egidio De Benedetto, Christian Demitri , Marta Madaghiele and Alessandro Sannino "Experimental Assessment of the Use of a Novel Superabsorbent polymer (SAP) for the Optimization of Water Consumption in Agricultural Irrigation Process"—Water 2014, 6, 2056-2069.
Deniz Aydemir, Alper Kiziltas, Gokhan Gunduz "Natural Fillers-filled Styrene-Maleic Anhydride Copolymer Composites"—Wood Research—60(1):2015, 167-174.

(Continued)

*Primary Examiner* — Marc S Zimmer
(74) *Attorney, Agent, or Firm* — FISHERBROYLES, LLP; Roger L. Browdy

(57) ABSTRACT

The invention describes a method for the production of a biodegradable superabsorbent composite polymer material, characterized by high absorbency under load. The invention also describes novel composite material made of styrene maleic acid copolymer preferably in salt form and a biopolymer, coated with biodegradable coating agents and cross-linked.

11 Claims, 4 Drawing Sheets

(56) References Cited

U.S. PATENT DOCUMENTS

| | | | | |
|---|---|---|---|---|
| 4,402,725 | A | 9/1983 | Heller et al. | |
| 4,418,163 | A | 11/1983 | Murakami et al. | |
| 4,468,343 | A | 8/1984 | Butler et al. | |
| 4,469,502 | A | 9/1984 | Heller et al. | |
| 4,483,950 | A | 11/1984 | Fanta et al. | |
| 4,500,670 | A | 2/1985 | McKinley et al. | |
| 4,666,983 | A | 5/1987 | Tsubakimoto et al. | |
| 4,698,404 | A | 10/1987 | Cramm et al. | |
| 4,703,108 | A | 10/1987 | Silver et al. | |
| 4,734,478 | A | 3/1988 | Tsubakimoto et al. | |
| 4,758,617 | A | 7/1988 | Tanioku et al. | |
| 4,771,105 | A | 9/1988 | Shirai et al. | |
| 4,820,773 | A | 4/1989 | Alexander et al. | |
| 4,824,901 | A | 4/1989 | Alexander et al. | |
| 4,855,179 | A | 8/1989 | Bourland et al. | |
| 4,888,238 | A | 12/1989 | Katz et al. | |
| 4,950,692 | A | 8/1990 | Lewis et al. | |
| 4,954,562 | A | 9/1990 | Anderson | |
| 4,963,638 | A | 10/1990 | Pazos et al. | |
| 4,971,954 | A | 11/1990 | Brodsky et al. | |
| 5,002,986 | A | 3/1991 | Fujiura et al. | |
| 5,013,349 | A | 5/1991 | Tanaka | |
| 5,026,784 | A | 6/1991 | Le-Khac | |
| 5,115,011 | A | 5/1992 | Harada et al. | |
| 5,221,787 | A | 6/1993 | Robison et al. | |
| 5,312,661 | A | 5/1994 | Suzuki et al. | |
| 5,340,853 | A | 8/1994 | Chmelir et al. | |
| 5,382,270 | A | 1/1995 | Graham et al. | |
| 5,385,729 | A | 1/1995 | Prencipe et al. | |
| 5,413,747 | A | 5/1995 | Akers et al. | |
| 5,447,727 | A | 9/1995 | Graham | |
| 5,525,682 | A | 6/1996 | Nagatomo et al. | |
| 5,572,827 | A | 11/1996 | Conrad | |
| 5,693,707 | A | 12/1997 | Cheng et al. | |
| 5,703,186 | A | 12/1997 | Sezi et al. | |
| 5,712,316 | A | 1/1998 | Dahmen et al. | |
| 5,720,736 | A | 2/1998 | Hatsuda et al. | |
| 5,733,576 | A | 3/1998 | Chmelir | |
| 5,733,994 | A | 3/1998 | Koepff et al. | |
| 5,791,085 | A | 8/1998 | Szmidt et al. | |
| 5,840,804 | A | 11/1998 | Carl et al. | |
| 5,846,214 | A | 12/1998 | Makuuchi et al. | |
| 5,847,089 | A | 12/1998 | Damodaran et al. | |
| 5,866,678 | A | 2/1999 | Kajikawa et al. | |
| 5,986,042 | A | 11/1999 | Irizato et al. | |
| 5,998,312 | A | 12/1999 | Kroesbergen | |
| 5,998,491 | A | 12/1999 | Haar, Jr. | |
| 5,998,492 | A | 12/1999 | Haar, Jr. et al. | |
| 6,060,557 | A | 5/2000 | Dahmen et al. | |
| 6,066,325 | A | 5/2000 | Wallace et al. | |
| 6,087,448 | A | 7/2000 | Mitchell et al. | |
| 6,309,454 | B1 | 10/2001 | Friedman et al. | |
| 6,310,105 | B1 | 10/2001 | Damodaran | |
| 6,326,446 | B2 | 12/2001 | Carter | |
| 6,342,652 | B1 | 1/2002 | Harada et al. | |
| 6,376,618 | B1 | 4/2002 | Mitchell et al. | |
| 6,410,616 | B1 | 6/2002 | Harada et al. | |
| 6,583,225 | B1 * | 6/2003 | Plochocka | C08L 73/02 525/193 |
| 6,630,422 | B1 | 10/2003 | Sannino et al. | |
| 6,660,819 | B2 | 12/2003 | Chmelir et al. | |
| 6,689,378 | B1 | 2/2004 | Sun et al. | |
| 6,710,141 | B1 | 3/2004 | Heide et al. | |
| 6,800,712 | B2 | 10/2004 | Doane et al. | |
| 6,821,331 | B2 | 11/2004 | Damodaran | |
| 6,833,488 | B2 | 12/2004 | Bucevschi et al. | |
| 7,009,020 | B2 | 3/2006 | Doane et al. | |
| 7,071,327 | B2 | 7/2006 | Mensitieri et al. | |
| 7,163,563 | B2 | 1/2007 | Schwartz et al. | |
| 7,166,356 | B2 | 1/2007 | Flohr | |
| 7,300,965 | B2 | 11/2007 | Weerawarna et al. | |
| 7,423,090 | B2 | 9/2008 | Doane et al. | |
| 7,423,106 | B2 | 9/2008 | Doane et al. | |
| 7,459,501 | B2 | 12/2008 | Doane et al. | |
| 7,985,819 | B2 | 7/2011 | Bucevschi et al. | |
| 8,013,083 | B2 | 9/2011 | Kosover et al. | |
| 8,022,140 | B2 | 9/2011 | Tikart et al. | |
| 8,378,022 | B2 | 2/2013 | Bucevschi et al. | |
| 8,596,931 | B2 | 12/2013 | Nagashima et al. | |
| 8,906,824 | B2 | 12/2014 | Loeker et al. | |
| 10,851,214 | B2 | 12/2020 | Medeiros et al. | |
| 12,128,144 | B2 * | 10/2024 | Bucevschi | C08F 212/08 |
| 2002/0193516 | A1 | 12/2002 | Bucevschi et al. | |
| 2004/0054341 | A1 | 3/2004 | Kellenberger et al. | |
| 2008/0227944 | A1 | 9/2008 | Ambrosio et al. | |
| 2009/0306290 | A1 | 12/2009 | Bucevschi et al. | |
| 2009/0324537 | A1 | 12/2009 | Bucevschi et al. | |
| 2010/0234233 | A1 | 9/2010 | Ambrosio et al. | |
| 2012/0267570 | A1 | 10/2012 | Shi et al. | |
| 2016/0316759 | A1 | 11/2016 | Bougoure et al. | |
| 2017/0051190 | A1 | 2/2017 | Zhang et al. | |
| 2018/0354869 | A1 | 12/2018 | Zhu et al. | |
| 2021/0187477 | A1 | 6/2021 | Bucevschi et al. | |
| 2023/0338207 | A1 | 10/2023 | Pannwitt et al. | |

FOREIGN PATENT DOCUMENTS

| | | | |
|---|---|---|---|
| EP | 317106 | A2 | 5/1989 |
| EP | 0722971 | B1 | 3/1993 |
| EP | 0722971 | A2 | 7/1996 |
| EP | 2277557 | | 6/2014 |
| EP | 2880116 | B1 | 2/2020 |
| GB | 929409 | A | 6/1963 |
| JP | H06122708 | A | 5/1994 |
| JP | 2004-339496 | A | 12/2004 |
| JP | 2006008800 | A | 1/2006 |
| WO | 2005/084724 | | 9/2005 |
| WO | 2006069732 | | 7/2006 |
| WO | 2007/115169 | | 10/2007 |
| WO | 2009/014824 | A1 | 1/2009 |
| WO | WO 2009/049105 | A2 * | 4/2009 |
| WO | 2008120742 | A1 | 7/2010 |
| WO | 2016/090330 | A1 | 6/2016 |
| WO | 2019195271 | A1 | 10/2019 |

OTHER PUBLICATIONS

Sahibi Belkhiria, Thhierry Mieyer, Albert Renken "Styrene Maleic Anhydride Copolymerization in a Recycle Tubular Reactor; Reactor stability and Product Quality"—Chemical Engineering Science. vol. 49, No. 248, pp. 4981-4990. (1994).

Steffen Jockusch, Nicholas J. Turro, Yoshiro Mitsukami, Makoto Matsumoto-"Photoinduced Surface Crosslinking of Superabsorbent Polymer Particles"—J Appl Polym Sci 111: 2163-2170, (2009).

Hossein Hosseinzadeh "Synthesis and swelling properties of a poly(vinyl alcohol)-based superabsorbing hydrogel"—Current Chemistry Letters 2 (2013) 153-158.

Roman Geier, Christina Wappl, Hilde Freiszmuth, Christian Slugovc and Georg Gescheidt "Thermal effects in polymerisations—a live view differentiating between bulk effects, thermal diffusion, and oxygen inhibition"- | Polym. Chem., 2015, 6, 2488-2492.

Z. Florjanczyk et al.(2000)"Lithium gel polyelectrolytes based on crosslinked maleic anhydride-styrene copolymer" Electrochimica Acta 45 (2000) 3563-3571.

Rakesh Singh et al (2013). "Biodegradation of Styrene-Butadiene-Styrene Copolymer via Sugars Attached to the Polymer Chain" Advances in Materials Physics and Chemistry, 2013, 3, 112-118.

Bakass M., Mokhlisse A., Lallemant M. [2002 "Absorption and Desorption of Liquid Water by a Superabsorbent Polymer: Effect of Polymer in the Drying of the Soil and the Quality of Certain Plants" J Appl Polym Sci vol. 83: 234-243.

Akhter J., Mahmood K., Malik K.A.,. Mardan A, Ahmad M., Iqbal M.M, [2004] Effects of hydrogel amendment on water storage of sandy loam and loam soils and seedling growth of barley, wheat and chickpea Plant Soil Environ. vol. 50: 463-469.

Yangyuoru M., Boateng E., Adiku S.G. ,KAcquah D. [2006] "Effects of Natural and Synthetic Soil Conditioners on Soil Moisture Retention and Maize Yield" West Africa Journal of Applied Ecology (WAJAE), vol. 9 : 1-8.

(56) References Cited

OTHER PUBLICATIONS

Wang Y.T. , Greg L.L. [1989]. "Hydrophilic polymers—their response to soil amendments and effect on properties of a soilless potting mix". J. Amer. Soc. Hort. Sci. vol. 115 : 943-948.
Puoci F., Iemma F., Spizzirri U. G., Cirillo G., Curcio M., Picci N. [2008] "Polymer in Agriculture: a Review" Am. J. Agri. Biol. Sci., vol. 3 : 299-314.
El Hady O.A., Tayel M.Y. ,Lofty A.A. [1981]. Super gel as a soil conditioner. II. Its effects on plant growth, enzyme activity, water use efficiency and nutrient uptake. Acta Horticulturae vol. 19 : 257-265.
Milimouk I., Hecht A.M., Beysens D., Geissler E. [2001] "Swelling of neutralized polyelectrolyte gels" Polymer vol. 42 : 487-494.
Zohuriaan-Mehr M. J., Kabiri K. [2008] "Superabsorbent Polymer Materials: A Review" Iranian Polymer Journal vol. 17 : 451-477.
Capezza Villa AJ, "Novel superabsorbent materials obtained from plant proteins" 2017. p. 28, Capezza Villa AJ. Dec. 31, 2017.

* cited by examiner

Biodegradation Test with Municipal Compost

Day-1

Day-2

Day-3

Day-4

Day-5

Degradation on non stirred solution (0.5wt% polymer) with light and air

O'Leary, N. D.; O'Connor, K. E.; Dobson, A. D. W., Biochemistry, genetics and physiology of microbial styrene degradation. *FEMS Microbiology Reviews* 2002, *26* (4), 403-417

PROCESS FOR THE PRODUCTION OF BIODEGRADABLE SUPERABSORBENT POLYMER WITH HIGH ABSORBENCY UNDER LOAD BASED ON STYRENE MALEIC ACID COPOLYMERS AND BIOPOLYMER

FIELD AND BACKGROUND OF THE INVENTION

The invention relates to a process for obtaining a biodegradable superabsorbent polymer (SAP) used in the manufacturing of diapers. More specifically, the invention relates to biodegradable SAP made from styrene maleic acid copolymer and biopolymers.

Superabsorbent polymers (SAPs) can absorb and retain extremely large amounts of a liquid relative to their own mass. Such water-absorbing polymers, that are classified as hydrogels when cross-linked, absorb aqueous solutions through hydrogen bonding with water molecules. A SAP's ability to absorb water depends on the ionic concentration of the aqueous solution. SAP materials used in manufacturing diapers are characterized of having a free absorbency to distillate water higher than 100 g/g.

A particular class of SAP used in manufacture of diapers is represented by those materials characterized by a high rate of free absorbency and a value of absorbency under load (AUL) higher than 20 g/g in salt solutions of 0.9% NaCl at a pressure of 0.9. Absorbency Under Load (AUL) characterization of SAP type materials are discussed in Bucholtz et al. (1998).

Biodegradable SAP materials belong to the following classes: a) materials consisting only of crosslinked biopolymers; b) materials consisting only of crosslinked synthetic polymers and c) composite materials consisting of synthetic polymers and biopolymers in certain variations: in inter crosslinking type connection without chemical agents; in crosslinking type connection with chemical agents; graft type; intercomplexate type and interpenetrate type. [Hoffman (2002)]

Copolymers such as for example styrene maleic acid are known in the art as SAP materials and various methods of copolymerization are known as well.

Von Bonin in U.S. Pat. No. 4,390,672 shows that maleic anhydride, which melts at 52° C., may be used as polymerization medium itself at temperatures above its melting point, in particular for copolymerization with methacrylic acid and derivatives thereof, without any uncontrollable reactions taking place which would result in unreproducible and unusable products. In the course of polymerization, maleic acid anhydride is built into the polymers and at the same time polymerization is controlled so that the polymers obtained are stirrable at temperatures below 200° C. This effect is enhanced in particular by the addition of so-called regulators. The following quantities are used, based on the total quantity of monomers put into the process, including also the maleic acid anhydride which initially serves as reaction medium: 90 to 20% by weight, preferably 75 to 30% by weight, of maleic acid anhydride and 10 to 80% by weight, preferably 20 to 70% by weight, of comonomers, at least 50% by weight, preferably 65% by weight of this quantity of comonomers.

In the method employed for polymerization, the molten maleic acid anhydride initially constitutes the polymerization medium. As polymerization progresses and most of the maleic acid anhydride initially present has been used up by copolymerization, the function of polymerization medium may be taken over by the polymer melt. Unreacted maleic acid anhydride may either be left in the product or removed by extraction or distillation. The same principle of synthesis is found in U.S. Pat. Nos. 2,479,522; 2,640,819; 2,855,387 or 5,221,787.

A disadvantage of the copolymerization of maleic anhydride with other monomers when the maleic anhydride it is also a reaction medium refers to the fact that the chemical process occurs at temperature higher than 150° C. and at high pressure conditions which in general generates polymers with low molecular mass.

The bulk copolymerization of maleic anhydride with different vinyl monomers inclusive styrene is accompanied by intense exothermic phenomena. Referring to this aspect, Sahiba Belkhiria et al (1994) show that the intensity of exothermic phenomenon can be diminished if the molar fraction of the styrene in the mass of reaction is smaller than 0.15, when also the styrene conversion to polymer is advanced (in the same conditions it can be obtained a conversion of styrene to polymer higher than 95%). The same principles are mentioned in: Z. Florjanczyk et al. (2000); D. M. G. Comissiong et al. (2007), U.S. Pat. Nos. 6,156,858; 7,009,011.

Bucevschi et al in U.S. Pat. No. 7,985,819 shows the preparation of styrene maleic acid copolymer based on the method which uses an excess of maleic anhydride as reaction medium with a ratio of styrene:maleic anhydride between 1:6 and 1:14 by weight, in which the styrene maleic anhydride polymer is soluble and then the polymer of maleic anhydride type is converted in acid type by its hydrolysis with water. Disadvantages of the synthesis procedure consists in: a) the exothermic process is controlled only through the intensity of heat transfer obtained by cooling the mass of reactants; b) a high consumption of water used to purify the polymer; c) efficiency of conversion of raw materials into the styrene maleic acid polymer is low.

Exothermic phenomena which occurs in the polymerization and copolymerization process is known in art. The control of this phenomenon is achieved by using inhibitors and retardants. [K. V. Middle, et al (2005); Roman Geier et al (2015); Nedal Y et al (2017); S. M. Rowe (1997) and U.S. Pat. Nos. 4,468,343; 2,996,480; 8,013,083; US 20080200616 or Z. Florjanczyk et al. (2000)"; Zbigniew Florjanczyk et al. (1998].

Preparation of SAP materials made of styrene maleic acid copolymers in the form of hydrogels and using carboxylate synthetic material is known in art. The chemical principles for their preparation refers in most cases to crosslinking of these polymers with different chemical agents from the category mentioned in U.S. Pat. No. 3,980,663, and as an example for the use of absorbent polymeric materials can be seen the following: U.S. Pat. Nos. 3,935,363; 3,954,721; 3,959,569; 3,980,663; 3,983,095; 4,041,228; 4,251,643; 5,026,784; 5,221,787 4,117,184; 4,500,670; 5,466,731; 4,167,464; 5,693,707; 4,855,179; 4,888,238; 4,076,917; 4,101,606; 6,087,448 or 8,022,140 and Hossein Hosseinzadeh (2013); Z. Florjanczyk et al. (2000); Zbigniew Florjanczyk et al. (1998). In the same class of materials are included and those resulted from carboxylate polymers, cross-linked with different polymers from which result composite polymeric materials as in: U.S. Pat. Nos. 5,385,729; 5,846,214; 6,689,378 or C. Demitri et al. (2013); S. M. Rowe (1997); Deniz Aydemir et al. (2015).

US20090324537 presents the preparation of a polymeric composite made from styrene maleic acid copolymer as salt with monovalent cations and gelatin which after drying is thermally cross-linked in two steps. After the second step of thermal crosslinking, an increase of water absorbency and swelling velocity is obtained in aqueous media.

The degree of crosslinking affects the absorbent capacity and gel strength of a SAP material. Absorbent capacity is a measure of the amount of fluid which a given amount of superabsorbent polymer will absorb. Gel strength indicates the tendency of the hydrogel once formed to deform under an applied stress. Polymers exhibiting inadequate gel strength will form a hydrogel which deforms and fills the void space in an absorbent article, inhibiting absorbent capacity and fluid distribution throughout the article. Polymers having low absorbent capacity are incapable of absorbing a sufficient amount of the fluid encountered in use of a diaper or other absorbent article. A polymer having a high gel strength generally possesses a low absorption capacity, and a polymer having a high absorption capacity typically possesses a low absorption rate because of gel blocking phenomenon or low gel strength after absorption. Another characteristic that a superabsorbent polymer must possess is an acceptable level of extractable polymer remaining within the SAP. The extractable polymer can leach out of a hydrogel when fluids contact the superabsorbent. The extractables that leach out of the superabsorbent apparently lower the absorption speed and capacity of the superabsorbent, resulting in leakage of the fluid from an absorbent article.

Most of the methods found in art discuss the surface cross-linking of polymeric materials which have three dimensional structure generated before the surface treatment and these can be seen in: U.S. Pat. Nos. 4,666,983; 4,734,478; 4,758,617; 4,820,773; 4,824,90; 4,954,562; 5,002,986; 7,166,356; 4,758,617; 4,771,105; 4,820,773; EP2277557A1 and respectively Enas M. Ahmed et al. (2015); Mohammad J. Zohuriaan-Mehr et al (2008); Steffen Jockusch et al. (2009)

A technical issue related to SAP material production which require AUL is referred to the products' granulometry and requires a particle size of polymer particles higher than 100 microns in the final product. The term "particle size" in the context of SAP materials that have particles of different geometrical forms, refers to an average diameter.

Biodegradable SAP materials are known, as can be seen in Raphael M. Ottenbrite et al. (1994); Enas M. Ahmed et al. (2015); Abraham J. Domb et al. (1997); Rajiv Dabhil et al. (2013); Fidelia N. Nnadi (2012); Alessandro Sannino et al (2009); Francesco F. Montesano et al. (2015); Fidelia Nnadi et al (2011) and U.S. Pat. Nos. 5,733,994; 5,847,089; US 20080227944; US20100139347; US20100234233. Regarding the biodegradability of material that include substance as styrene see: Rakesh Singh et al (2013); P. Galgali et al (2004); Niall D. O'Leary et al (2002).

SAP materials obtained from styrene-maleic anhydride copolymers and biopolymers such as gelatin are known in art as: U.S. Pat. Nos. 6,833,488; 8,378,022; US20090324537 at which the biodegradation is evaluated versus the enzyme from the gastro-intestinal tract.

SUMMARY OF THE INVENTION

The invention discloses a new and improved method for production of superabsorbent polymers (SAP) used in the manufacture of diapers that are biodegradable and have a high absorbency under load (AUL).

The invention also discloses a method for the production of a composite polymeric material based on synthetic polymer and natural polymer, the composite having a 3D macromolecular configuration. The composite material may be either crosslinked or non-crosslinked. When non-crosslinked, the polymeric composite material (usually in granular form) may be treated with coating agents and subsequently exposed to thermal treatment (in one step or two or more steps) that lead to conversion of non-crosslinked polymeric composite to a crosslinked polymeric composite with a three dimensional macromolecular configuration and high absorbency under load.

In a preferred embodiment, the polymeric composite material is biodegradable. In another preferred embodiment the method generates as end product a single solid phase with granulometric size characteristic for using in diapers. Granulometric size refers to the average diameter of grains in SAP.

Alternatively, two solid phases are obtained: a small solid phase (SSP), with particles size not higher than 100 microns, that can be recycled; and a large solid phase (LSP) with particle size higher than 100 microns, preferably between 100 and 850 microns.

In a preferred embodiment the SAP material is made of styrene maleic anhydride copolymer (SMA) by bulk copolymerization using an excess of maleic anhydride to styrene, whereas maleic anhydride functions as a solvent for the resulted polymer.

In a further aspect the invention provides a biodegradable polymeric composite represented by the formula:

$$\{[\mathrm{SMAC}^{(-)}D^{(+)}B]S]\}W, \text{ wherein:}$$

SMAC− represents a styrene maleic acid copolymer in acid form or anionic form;

D represents a counterion when SMAC is in anionic form;

B represents a biopolymer selected from a protein, soybean protein, collagen, collagenic biopolymer, gelatin, collagen hydrolysate, albumin, guar or starch and casein, S represents coating agent selected from glycerin, ethylene glycol, propylene glycol, polyethylene glycol or polyether hydroxyl W represents water bonded to the composite;

the polymeric composite having an absorbency under load (AUL) that is higher than 20 g/g in aqueous solution of 0.9% NaCl at pressure of 0.9 psi.

In a preferred embodiment B is gelatin and D is selected from $Li^{(+)}$, $Na^{(+)}$, $K^{(+)}$, and $NH_4^{(+)}$.

In another preferred embodiment the amount of B relative to SMAC in the composite is at least 4-6% (dry basis), preferably at least 8-10% (dry basis) and more preferably the amount of B relative to SMAC in the composite is at least 12-14% (dry basis).

In another aspect the invention provides a method of preparing a biodegradable polymeric composite having an absorbency under load (AUL) that is higher than 20 g/g in aqueous solution of 0.9% NaCl, comprising:

a) preparing an aqueous solution of a synthetic copolymer of styrene-maleic acid;

b) preparing an aqueous solution of an inorganic base c) preparing an aqueous solution of a biopolymer;

d) mixing the copolymer solution from step a) with the inorganic base solution from step b) to form polymer-inorganic salt;

e) adding the aqueous biopolymer solution from step c) to the polymer-inorganic salt of step d) to form an aqueous polymeric mixture;

f) drying and grinding the polymeric mixture obtained in e) to obtain at least one solid phase polymeric material characterized by particle size of 100 microns or higher, preferably of 100-850 microns;

g) coating the polymeric material of f) with a compound with properties of biodegradability selected from glycerin, ethylene glycol, propylene glycol, polyethylene glycol or polyether hydroxyl, h) thermally crosslinking the polymeric material of step g) to form biodegradable composite polymer with an absorbency under load (AUL) that is higher than 20 g/g.

In another aspect the invention provides a biodegradable polymeric composite represented by the formula:

$$\{[VMAC^{(-)}D^{(+)}B]S]\}W, \text{ wherein:}$$

VMAC-represents a copolymer of methyl vinyl ether, vinyl chloride or vinyl acetate with maleic acid in acid form or anionic form;

D represents a counterion when VMAC is in anionic form;

B represents a biopolymer selected from a protein, soybean protein, collagen, collagenic biopolymer, gelatin, collagen hydrolysate, albumin, guar or starch and casein, S represents coating agent selected from glycerin, ethylene glycol, propylene glycol, polyethylene glycol or polyether hydroxyl W represents water bonded to the composite;

the polymeric composite having an absorbency under load (AUL) that is higher than 20 g/g in aqueous solution of 0.9% NaCl at pressure of 0.9 psi.

BRIEF DESCRIPTION OF THE DRAWINGS

The invention will now be described with reference to the drawings, wherein.

DETAILED DESCRIPTION OF THE INVENTION

This invention presents a method for production of a biodegradable superabsorbent composite polymer with high absorbency under load (AUL). The composite polymer of the invention comprises a synthetic hydrophobic polymer and a natural biopolymer. More specifically, the composite polymer comprises styrene maleic acid copolymer and a biopolymer of animal or vegetal origin in conformity with the technological flow chart presented in FIG. 1. Styrene maleic acid copolymer is preferably in salt form, more preferably in the form of monovalent cation salt.

Alternatively, the styrene moiety in the synthetic polymer can be replaced by other hydrophobic moieties. Exemplary synthetic polymers are: poly(maleic anhydride-co-methyl vinyl ether) (Gantrez), poly(vinyl chloride-co-maleic acid) and poly[(maleic anhydride)-alt-(vinyl acetate).

The term "composite" as herein used refers to a polymeric substance that a) is formed from at least two polymers with different macromolecular chemical structure; and b) the resulting composite is a unique entity that does not separate spontaneously to its components during application. It is understood that the term "composite" may include other substances such as drugs, stimulators, inhibitors, odorants, emollients, plasticizer and others.

The term "anionic" refers to a polymeric composite generating in aqueous media a negative electrochemical potential as the result of the presence in its structure of some free acid functional groups capable of dissociating into anions.

Figure 1:
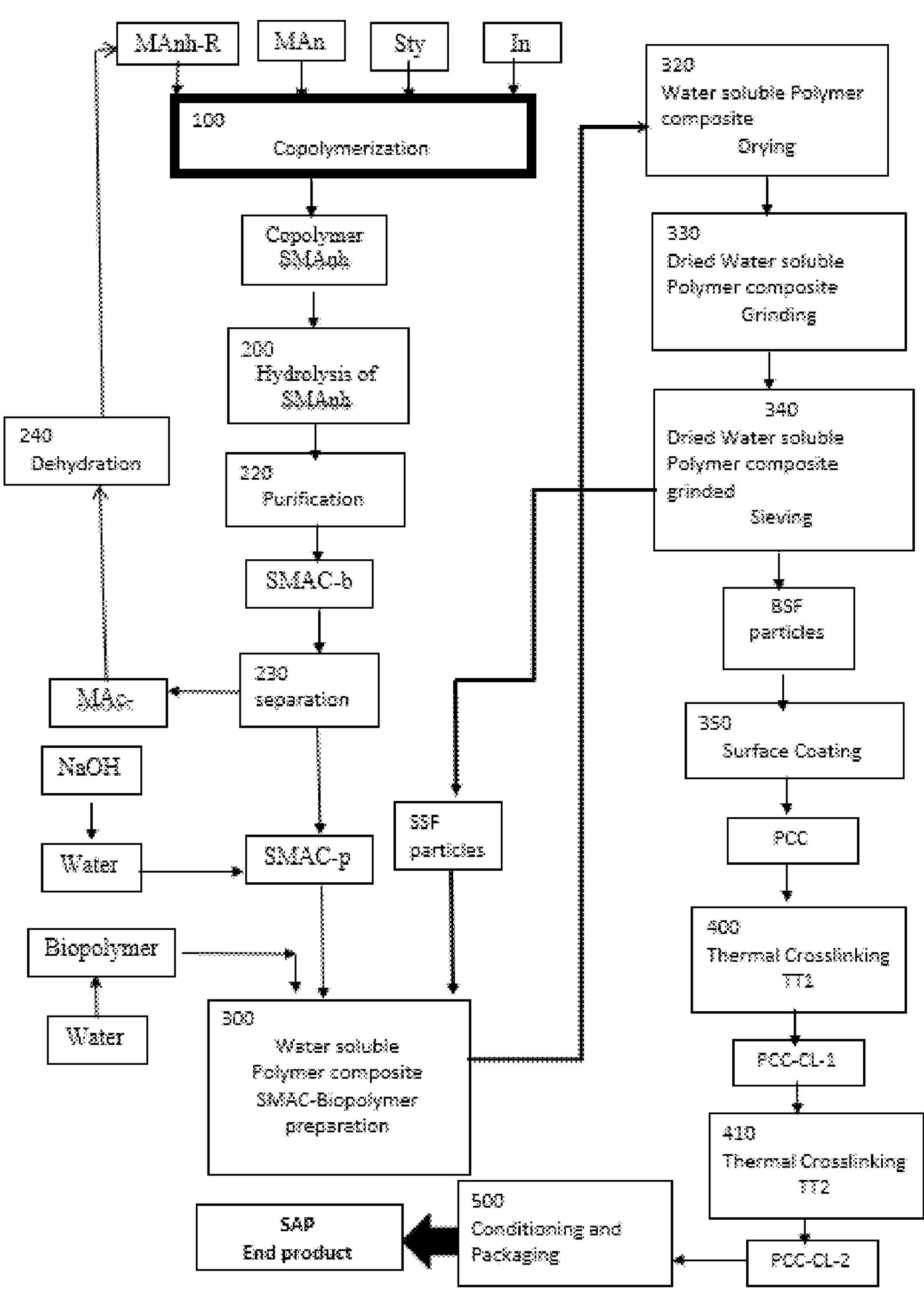
FIG. 1. Flow Chart of a manufacturing process of biodegradable SAP with high AUL FIG. 2. Synthesis of polystyrene maleic acid copolymer by bulk copolymerization: a) evolution in time of some properties of the mass of reaction (the graphs in the left when is evidenced the following: temperature of reaction mass in time with the point when occurs the exothermic step, the dosing of water volume added in time and the viscosity of reaction mass in time); b) images from Sigma mixer of 60 Liters in different moments of copolymerization in the right, are presented the images to understand the texture of the reaction mass in correlation with the graphic representation.

In an embodiment of the invention described in FIG. 1, the production process starts with the synthesis of copolymer (styrene-alt-maleic anhydride) by bulk co-polymerization using an excess of about 60-90% of maleic anhydride relative to styrene, whereas maleic anhydride works also as a solvent (operation 100).

Copolymerization is executed in Sigma-type mixer machines named Hermetic machines in order to be able to work at high pressures e.g. not exceeding 10 bar or in vacuum conditions (less than 10 mbar) with double mantle as well with arms equipped with a heating-cooling system.

The copolymerization process for the production of a superabsorbent polymer uses styrene monomer stabilized with organic compounds that inhibit the process of homopolymerization during storage and transportation. Such inhibitors are for example substances such as: amino derivatives, thiols derivatives, and hydroxyl derivates as for example (2-hydroxypropyl)-ethylene diamine compounds, 4-tert-butylcatechol and others) being preferred 4-tert-butylcatechol in proportion of 0.002-0.008% to the monomer, more preferably is 0.003-0.007% to the styrene and most preferably 0.004-0.006% to the styrene and the molar fraction of styrene in the reaction mass is 0.05-0.08, preferably 0.1-0.15 and more preferably 0.18-0.21.

The copolymerization also contains maleic anhydride that is either fresh maleic anhydride MAnh or recovered maleic anhydride MAnh-R that is recycled from a previous batch as schematically showed in FIG. 1. and the amount of fresh maleic anhydride MAnh relative to recovered maleic anhydride MAnh-R is about 10-40% (dry basis).

For copolymerization are used customary agents as peroxides, azo compounds etc., which form free radicals by thermal decomposition, while the quantity of initiator is 0.05-0.15%, preferably 0.07-0.009% and most preferably 0.08-0.12% to a double quantity of styrene adopted for copolymerization.

Next, it follows the conversion of styrene-alt maleic anhydride copolymer to styrene-alt maleic acid copolymer by hydrolysis with water (process 200) which is done in the same equipment where copolymerization has been made.

Conversion of styrene-alt maleic anhydride copolymer to styrene-alt maleic acid copolymer by hydrolysis using a quantity of water higher than the one stoichiometrical required for total hydrolysis (Ws) with an excess which represents 2-3% versus to the stoichiometrical value, preferably in excess of 4-5% to the stoichiometrical water and most preferably 5-10% in excess to the stoichiometrical water.

The total quantity of water necessary to styrene and maleic anhydride copolymer's hydrolysis is inserted in the mass of reaction in two steps from which 50% is in the form of 0.005N hydrochloric acid solution and the rest as non-acidulated water.

The acidulated water is inserted into the reaction mass in two portions at a mass reaction's temperature that not exceeding 60° C. at 15 minutes intervals between each dosage, and the quantity of non-acidulated water is inserted into the mass of reaction also in two portions, from which the first is after 60 minutes from the last portion of acidulated water, then is inserted the last portion of non-acidulated water and mixing of reaction mass for 45-60 minutes in cooling conditions of 35-40° C.

Reaction mass resulted after hydrolysis is a wet solid in form of a powdery mass of white color with a value of bulk density of 0.6-0.8 g/cm$^3$.

Further, mass of reaction that resulted after copolymerization and hydrolysis (which is a blend of styrene maleic acid copolymer-SMAC and free maleic acid-MAC, which contains traces amounts of non-reacted styrene and stabilizer for styrene as well as traces of hydrochloric acid) is transferred to perform the purification process of styrene maleic acid copolymer (process 220).

The purification process which represents the extraction of free maleic acid fraction from SMAC polymer mass is done in an equipment as tank-type with mixing in which over reaction mass resulted after hydrolysis of synthetic copolymer is added a quantity of deionized water for purification [Wp] that represents a quantity correlated to the wet mass of reactions (RM) in accordance with the relationship $W_p$=2*RM or $W_p$=5*RM, preferably $W_p$=3*RM.

Purification consists of 3-5 extraction stages followed each time by filtration. The number of extraction and filtration operations are established so that the content of the free carboxylic groups found in polymer of SMAC to be between 0.00909-0.0095 mole/gram, preferably between 0.0091-0.0094 mole/gram and most preferably between 0.0092-0.0093 mole/gram.

The extraction in fact occurs at temperature of 60° C. for 30 minutes and each filtration (process 230) is done with known equipment as press filter or Nuce filter. All solutions resulted from filtering are collected into a tank of supernatant in order to process the maleic acid which it contain.

Processing of maleic acid water solution to recovery of maleic anhydride consists of the following operations:

a) concentration of maleic acid solution through reverse osmosis;
b) spray drying of maleic acid concentrated solution when resulted maleic acid powder and water
c) conversion of maleic acid powder to maleic anhydride by thermal-vacuum dehydration (with technological parameters modified than those mentioned in U.S. Pat. No. 4,414,398) when in the end is obtained a material called recovered maleic anhydride (MAnh-R).

The purified filtrate of SMAC polymer is collected in an equipment as Sigma mixer type in order to be processed with biopolymers to obtain the water soluble composite polymer containing synthetic SMAC polymer and biopolymer [WSPC] (process 300).

The preparation process of polymeric composite [WSPC] containing SMAC and a biopolymer of animal or vegetal origin is preceded by other operations as follows:

a) Preparation of a base solution is obtained by dissolution of a solid hydroxide compound in water to 40% by weight, whereas examples of preferred base hydroxide compounds are sodium hydroxide, lithium hydroxide, potassium hydroxide, ammonium hydroxide, preferably sodium hydroxide.
b) transformation of styrene maleic acid copolymer obtained in step 230 into styrene-maleic acid monovalent cation salt by neutralization with base solution prepared in a) above in order to obtain a solution of copolymer salt with concentration higher than 25% preferably higher than 35% and most preferably higher than 50%. Neutralization of the SMAC copolymer is 48-58%, preferably 50-56% and most preferably 52-54%.
c) preparation of the biopolymer (as gelatin, albumin, casein, soy, guar or starch, preferably is gelatin) as water solution of 40% by weight in water;
d) preparation of polymeric composite is done by treating the solution of styrene maleic acid salt with biopolymer solution at temperature of 55-75° C. for 30 minutes.

The amount of biopolymer relative to copolymer in composite is 4-6% (dry basis), preferably 8-10% (dry basis) and most preferably 12-14% (dry basis).

The blending of the composite mass continues during 4-5 hours until the polymeric mass is transformed from the viscous solution into a partially dried granular mass with a moisture content not higher than 20%.

This partially dried polymeric composite material WSPC in granular form is subjected to supplementary drying (process 320) at temperatures of 75-85° C. on conveyor belt type or Rotary type in order to obtain final drying of until the moisture content is less than 14%, preferably less than 12% and most preferably less than 8%.

Further steps of drying, grinding and sieving are carried (process 330+process 340) to obtain two types of solid phases called herein large solid phase (LSP) with granulometric distribution higher than 100 microns, preferably of 100-850 microns that corresponds to be used in the manufacture of diapers and a small solid phase (SSF) with granulometric distribution up to 100 microns. The small solid phase SSF is re-used in the preparation of the next new batch of SAP who attended the process 300.

Further, the large solid phase LSP is exposed to post-treatment surface coating process using known chemical substances as: glycerin ethylene glycol, propylene glycol or polyether hydroxyl with properties of biodegradability. Examples of preferred coating materials are hydroxyl polyether, more preferably polyethylene glycol-PEG 200 used at a rate of 0.2-2% by weight (dry basis) to LSP, preferably at a rate of 0.5-1.5% by weight and most preferably at a rate of 0.8-1.2% by weight to LSP.

Surface coating is made in equipments as powder coating machines type at temperature of 30-70° C., preferably at temperatures of 35-65° C. and most preferably at temperatures of 40-60° C. for 30-90 minutes, preferably for 40-75 minutes and most preferably for 50-60 minutes. As a result of this process is resulted the material called Polymer Composite Coated Treated-PCC (operation 350).

The obtained material after surface coating (Polymer Composite Coated) is subdue to a thermal treatment called first thermal treatment (TT1) (operation 400) consisting in warming of particles mass in hot air with temperature of 90-140° C. for 30-150 minutes, preferably with temperatures of 100-135° C. for 45-120 minutes and most preferably by bulk thermal crosslinking at temperatures of 110-120° C., for 60-90 minute. using equipment of conveyor belt type or shaking rotary type when is resulted an intermediary material called Polymer Composite Coated first crosslinked (PCC-CL-1).

The material PCC-CL-1 is subdue to a new thermal treatment (TT2) (operation 410) in hot air with temperature of 120-150° C. for 5-30 minutes, preferably at temperatures of 125-145° C. for 10-25 minutes and most preferably to temperature of 120-140° C. for 15-20 minute in the same type of equipment used for TT1 and is obtained the Polymer Composite Coated second crosslinked (PCC-CL-2).

The material (PCC-CL-2) is then conditioned for 24 hours in an atmosphere in which the air has a moisture content of 65% and temperature of 20° C. and then is packaged in sealed polyethylene bags (operation 500).

The material resulted after conditioning is a biodegradable SAP with AUL higher than 20 g/g in aqueous solution of 0.9% NaCl at pressure of 0.9 psi, which represents the end product of the manufacturing process which is the object of the present invention.

Example 1

This example shows a representative variant for production of 10 kg biodegradable SAP with high AUL which is within the object of the present invention.

In a Sigma mixer (60 L) connected to vacuum, with a heating-cooling mantle, thermometer, and dosing funnel for liquids is inserted 2.59 kg of maleic anhydride technical grade (MAnh) and 12.07 kg recovered maleic anhydride (MAnh-R) from a previous batch. The solid mass is heated at temperature of 60° C. under mixing conditions until a homogenous transparent liquid is obtained which represents melted maleic anhydride. Then, 3.17 L of styrene containing 0.2016 g of 4-tert-butylcatechol as stabilizer and 5.04 g of benzoyl peroxide (BPO) as initiator (prepared in advance) are added in the mixer by using a dosing funnel at temperature of 5° C. After about 5 minutes from the styrene dosing, the reaction mass returns to a temperature of 60° C. After about 30 minutes at the same temperature begin the process of copolymerization, noted by increase of the temperature of the reaction mass with a speed of 0.2 degree/minute. When the mass of reaction reaches the temperature of 68° C., the reaction mass is cooled, by using a cooling agent with temperature of −8° C., after about 5 minutes the reaction mass reaches the temperature of 123° C. and then begins to decrease. In this moment the cooling is stopped and when the reaction mass reaches a temperature of 100° C., a heating aid is inserted in the mixer's mantle to maintain the temperature of reaction mass at 100° C. for 30 minutes. The reaction mass is then cooled to a temperature of 80° C. From this moment begins the developing of hydrolysis process of the maleic anhydride included in the polymer of SMA and also the free maleic anhydride, both being converted to maleic acid. The hydrolysis process occurs also in Sigma mixer by addition of 3.3 L of water in total, from which 1.6 L as 0.05N hydrochloric acid solution in two equal servings at 15 minutes interval and the rest of 1.7 L as deionized water which does not contain hydrochloric acid, inserted also in two servings at 60 minutes interval.

Figure 2:
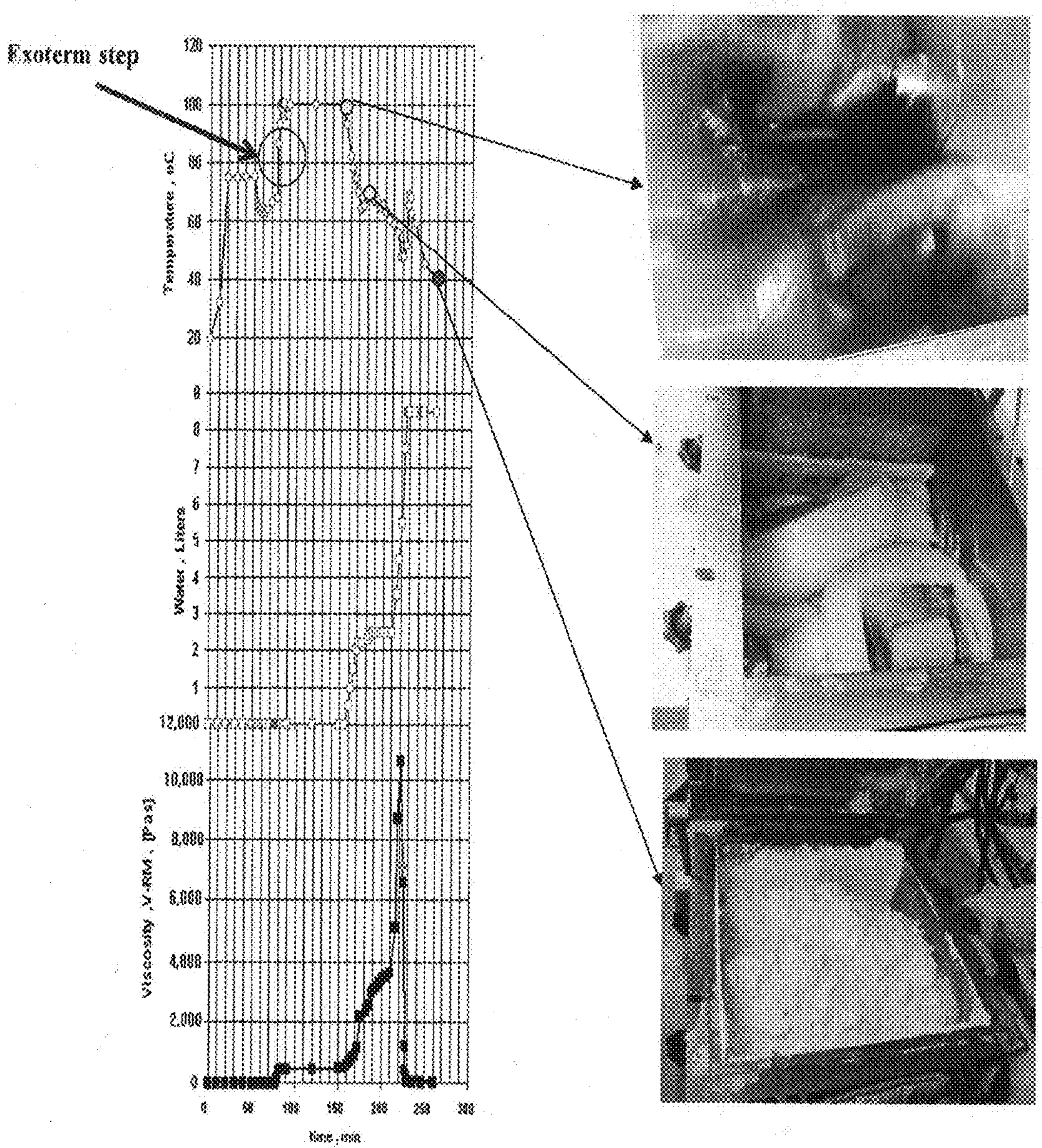

Variation in time of some properties and the aspect of the reaction mass from the moment when begins the copolymerization and to the end of the hydrolysis of the maleic anhydride free and linked to the copolymer SMAC are presented in FIG. 2.

Further the whole quantity of wet solid obtained after copolymerization and hydrolysis which represents 26.35 Kg is subdue to a process of separation of the copolymer styrene-alt maleic acid SMAC and its purification by successive extractions and filtrations using a Nuce filter with stirrer. For this purpose, over the quantity of 26.35 kg of wet reaction mass obtained in Sigma mixer is added 63 L of deionized water. The washing process occurs at temperature of 60° C. for 30 minutes, then the resulted suspension is filtered under pressure of 1.1 atm. It resulted 60 L of supernatant and 28 kg filtrate. The filtrate as wet solid is subdue to a new extractions with 63 L of deionized water, the suspensions resulted is mixed at 60° C. for 60 minutes. After this second filtration are obtained 31 kg filtrate and 59 L of supernatant.

Whole quantity of 119 L supernatant shall be further processed for recovery of maleic acid which it contains and then its converting in maleic anhydride necessary to the new batch of synthetic polymer. After the concentration of supernatant by reverse osmosis from 15% to 30%, further is subdue to atomization to obtain the maleic acid. In the end by thermal dehydration under vacuum (by modifying the method described in U.S. Pat. No. 4,414,398) are obtained 12.07 kg of recovered maleic anhydride (MAnh-R].

The wet solid mass of 31 kg that represents the filtrate is transferred in Sigma mixer to prepare the polymeric composite following addition of the biopolymer. This process occurs as follow: in Sigma mixer over 31 kg of wet SMAC is added 4.52. L of NaOH solution of 40% concentration, and is obtained a quantity of 35.52 kg of viscous mass that represents styrene maleic acid copolymer as sodium salt of 16.37% concentration.

Separately in a reaction vessel with stirrer and heating-cooling mantle, 1.28 L of gelatin Type A (Bloom 150) solution of 20% concentration is prepared.

Finally in Sigma mixer is mixed at a temperature of 65° C. for 2 hours 35.52 kg solution of synthetic polymer with 1.28 L of gelatin solution to which is added also 1.83 kg of small solid phase of SAP resulted from a previous batch. Further the homogenous mass from mixer is dehydrating under vacuum of 10 mbar for 5 hours when its humidity content reaches 23.4% and the mass has a granular aspect called WSPC (water soluble polymer composite).

Instead of poly(styrene-maleic acid) copolymer, other synthetic polymers are used, for example poly(maleic anhydride-co-methyl vinyl ether) (Gantrez), poly(vinyl chloride-co-maleic acid) and poly[(maleic anhydride)-alt-(vinyl acetate).

The polymeric material WSPC that results after preparation is subdue to a supplementary drying. In this sense occurs the transport of granular mass of partial dried composite to a dryer with pre-heated air at temperature of 75-85° C. as rotary type and is dried until the humidity content will be less than 7.44%.

Further the WSPC supplementary dried is grinded and sieved in several steps so in the end are obtained two types of solid phases called big solid phase BSF and small solid phase SSF (with the biggest particle under 100 microns). By grinding with conical mills are obtained 1.83 kg SSF and 8.1 kg of LSP with the granulometric distribution presented in Table-1.

The 8.1 kg of LSP are coated with 0.07 kg of PEG-200 solution during 90 minutes at temperature of 45° C.

The coated product is subdue to a thermal treatment at temperature of 110° C. during 90 minutes (TT1), when is obtained the material PCC-CL-1 which is let to cool until it reaches a temperature of 40° C. Then is subdue to a second thermal treatment which occurs at temperature of 130° C. for 15 minutes. After cooling and conditioning at room temperature are obtained 10 kg SAP.

According to the production process presented in this example has been done 3 batches to test the reproducibility of the technology. The results of the technical characteristics of SAP materials resulted in conformity with the present invention are shown in Table-1.

TABLE 1

Technical characteristics of the 3 batches of AP material in conformity with Example 1

| Property | | Analytical Value | Min. | Max. | Methods |
|---|---|---|---|---|---|
| Appearance | | white-yellow granules | | | |
| Moisture % | | 4.5 | 4 | 6 | ISO 17190-4-2001 |
| Apparent Bulk Density | (g/cm3) | 0.72 | 0.64 | 0.76 | 460.2-02 |
| Particles Size: LSP | (%) | | | | ISO 17190-3-2001 |
| >850 | (microns) | 0.5 | 0.2 | 1 | |
| 850-500 | (microns) | 28 | 20 | 45 | |
| 500-250 | (microns) | 61.5 | 55 | 70 | |
| 150-250 | (microns) | 10 | 5 | 12 | |
| Particles Size: SSF | (%) | | | | ISO 17190-3-2001 |
| <150 | (microns) | — | — | — | |
| Residual Monomers | | N/D | N/D | N/D | ISO 17190-2-2001 |
| Ph | | 6.8 | 6.5 | 7 | ISO 17190-1-2001 |
| Free absorbency | (g/g) | 50 | 44 | 52 | ISO 17190-5-2001 |
| Centrifuge Retention Capacity | {g/g} | 34 | 28 | 35 | ISO 1790-6-2001 |
| Absorbency Under Load 0.3 psi | (g/g) | 31 | 29 | 33 | ISO 17190-7-2001 |
| AUL 0.6 psi | (g/g) | 27 | 24 | 28 | ISO 17190-7-2001 442.2-02 |
| AUL 0.9 psi | (g/g) | 22 | 19 | 22 | ISO 17190-7-2001 |

The test methods are in conformity with ISO 171901-2001

Example-2

This example presents the biodegradation test of SAP material obtained in Example-1 by using as biodegradation medium the municipal compost.

Figure 3:
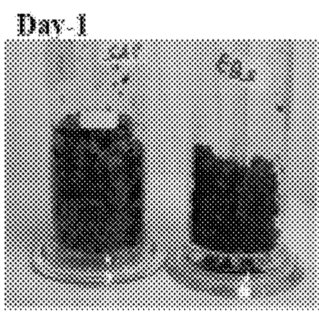
FIG. 3. Images showing the biodegradation test of commercial polyacrylate superabsorbent polymer SAP vs. that of the biodegradable polymeric composite of the present invention termed EBS, during the biodegradation test with municipal compost. The images clearly show the appearance of carbon dioxide and decrease in the sample's mass because of its digestion by the bacteria which exist in municipal compost in the case of EBS. This phenomena is not observed in the case of commercial SAP.
Figure 3:
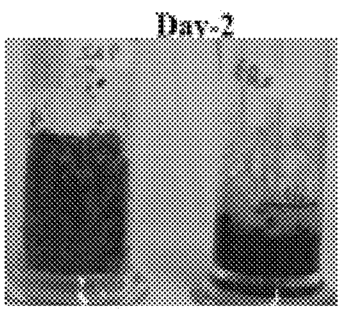
Figure 3:
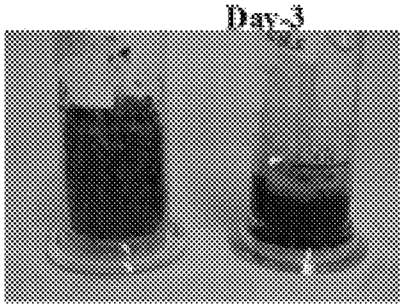
Figure 3:
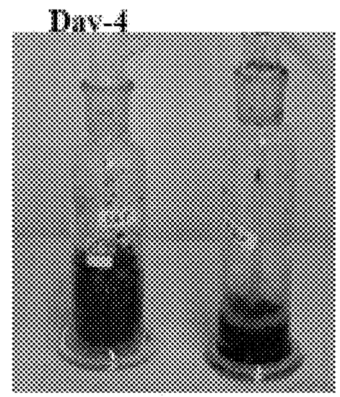
Figure 3:
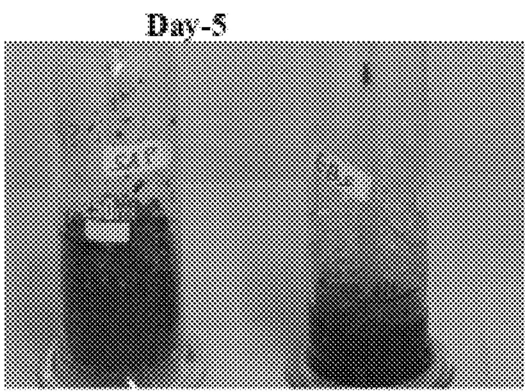

The objective of this experiment is to evaluate the biodegradability of the two polymers—SAP material obtained by the method of the present invention as disclosed in Example 1 and just for ease of comparison, referring in this example and in FIG. 3 as to EBS and commercial SAP material polyacrylate based. The test will be based on the proposed new guideline by the Organization for Economic Cooperation and Development (OECD 310) and on the US EPA OPPTS guideline 835.3120. The test, $CO_2$ in sealed vessels (headspace test), is suitable for testing insoluble substances [Organization for Economic Cooperation and Development (OECD) (October 2003): Proposal for a new guideline 310 for Testing of Chemicals: Ready biodegradability—$CO_2$ in sealed vessels (Headspace test).

Principle of the Test

When testing for the ultimate biodegradability of insoluble substances or substances for which a homogenous solution cannot be obtained, the methods of choice are the respirometric methods where $CO_2$ evolution or $O_2$ consumption are measured. The present test is based on measurement of $CO_2$ produced during the ultimate biodegradation of the tested substances. The test substance, at approximately 20 mgC/L, as the sole source of carbon and energy, is incubated in a buffer-mineral salts medium which has been inoculated with a mixed population of microorganisms. The test is performed in sealed bottles with a headspace of air, which provides a reservoir of oxygen for aerobic biodegradation. The $CO_2$ evolution, resulting from the ultimate aerobic biodegradation of the test substance, is determined in the test bottles in excess of the $CO_2$ produced in the blank vessels containing inoculated medium only. The $CO_2$ values are translated to equivalent inorganic carbon (IC) produced and the extent of biodegradation is expressed as the percentage of the maximum theoretical IC (ThIC) production, based on the quantity of test substance (as organic carbon) added initially. A few controls are run in parallel: (1) Blank control, containing inoculum and mineral medium, but no test compound, (2) Procedure control, containing a reference biodegradable substance (sodium benzoate) and, (3) Inhibition controls, containing both the test and reference substances, in order to check possible inhibition to the microorganisms, and (4) abiotic controls, where the inoculum is poisoned by mercuric chloride ($HgCl_2$).

The test is normally run for a period of 28 days but may be prolonged if degradation has begun by day 28. Biodegradation of >60% ThIC within a '10-d window' (the 10 days following the attainment of 10% biodegradation) in the test, demonstrates that the test substance is readily biodegradable under aerobic conditions The substances to be tested are the two super absorbent polymers Experimental Bio SAP (EBS) and commercial polyacrylate superabsorbent polymer (SAP). Elemental analysis of the polymers will be performed in order to determine carbon content.

Test Substances

The substances to be tested are the two super absorbent polymers EBS that is the composite polymer of the present invention and commercial SAP. Elemental analysis of the polymers will be performed in order to determine carbon content.

Reference Substance

In order to check the functional capability of the activated sludge and the possible inhibitory effect of the polymers, a control with a reference substance will be run in parallel. The reference substance that will be used is sodium benzoate ($C_7H_5NaO_2$).

Water for dilutions will be prepared by sparging overnight distilled water at pH 6.5 with $CO_2$ free air. The $CO_2$ free air will be prepared by passing air through soda lime pellets.

Mineral medium will be prepared from the stock solutions (a), (b), (c), (d).

The inoculum will consist of activated sludge collected at a Haifa Municipal Wastewater Treatment Plant. In order to reduce $CO_2$ background levels, the sludge will be aerated for a few days (no longer than 7 days) before using it for the test.

Test Procedure

Aliquots of 100 ml inoculated medium will be dispensed into replicate bottles of 160-ml capacity, leaving a headspace of 60 ml. The number of bottles in each set will be such that at each sampling time, three bottles can be sacrificed.

Sampling

Following acidification of the medium (4.5.4), a sample of 1 ml will be withdrawn from the headspace and injected into the gas chromatograph (GC) for the determination of $CO_2$ concentration. The sampling schedule will depend on the lag period and rate of biodegradation of the test substance. Three bottles will be sacrificed for analysis on each day of sampling, which will be approximately once every 5 days. The test should normally run for 28 days but might be prolonged if degradation has begun by day 28. Bottles representing the inhibition and abiotic controls will be sampled only on day 1 and 28 (or last day).

Calculation of Results

Assuming 100% mineralization of the test substance to $CO_2$, the maximum IC production (ThIC) in excess of blank production equals the amount of total organic carbon (TOC) contributed by the test substance added to each bottle. The total mass of inorganic carbon (TIC) in each bottle is the summation of the mass in the liquid and the mass in the headspace. Since the standards were prepared from defined IC solutions that were acidified and treated like the test samples, each standard represents a specific carbon concentration in solution after equilibration with gaseous phase. Consequently, the TIC mass in the reaction mixtures equals the carbon concentration value obtained by the GC analysis multiplied by the liquid volume.

The percentage of biodegradation (% D) is given by the following equation:

$$\%\ D=(TIC_t-TIC_b)/TOC\times 100$$

where:

$TIC_t$=mg TIC in test bottle at time t $TIC_b$=mean mg TIC in blank bottles at time t TOC=mg TOC added initially to the test vessel Results The results from the first five days of the test are presented in Table 2. In the procedure control, a net 16% of carbon was released as $CO_2$. In the EBS test, 7% of carbon was released as $CO_2$ while in the SAP test there was not net release of $CO_2$. It should be mentioned that at this point, the amount of $CO_2$ released in the SAP samples was less than the amount released by the blank control where the background $CO_2$ production by the inoculum was measured.

TABLE 2

| Biodegradation of the polymers during first five days of test | | | |
|---|---|---|---|
| | ThIC (mg/L) | IC (mg/L) | % IC$^c$ produced |
| Blank | 0 | 0.9 | NA |
| Procedure control | 35 | 6.4 | 16 |
| EBS-test | 21 | 2.3 | 7 |
| SAP-test | 19.5 | 0.6 | 0 |

ThIC concentrations are calculated from average weight of polymers introduced in the bottles sacrificed at the specific time points—Average production of $CO_2$ from the same sacrificed bottles was translated to IC according to calculations Percent degradation was calculated after deduction of blank. NA—not applicable The evolution in time of the biodegradation test is presented in the images shown in FIG. 3.

Example-3

This example presents a biodegradation test of SAP prepared as in example-1 except that the gelatin content is 10% and the biodegradation medium used are the soils extract.

We have tested the biodegradability of the heteropolymer polystyrene-maleic anhydride-gelatine (SMA-G) after incubation with 3 bacterial cultures.

Polymer: SMA containing 10% of gelatine

Bacteria: 2 bacterial strains and a mixed bacterial population (consortium) isolated from soil after 2 weeks incubation of soil samples with a solution of the polymer.

Biodegradation tests: 100 mg of dry polymer were added to 50 ml mineral synthetic medium in 250 ml flasks. This medium was inoculated with the bacteria mentioned above and incubated on a rotary shaker at 30 C, for periods of 2 weeks for testing the degradation of the gelatine and for a period of 8 weeks for testing the dry weight of the residual synthetic polymer.

a) Biodegradation of the gelatine constituent was determined by the Biuret method after 1 and 2 weeks of incubation b) Biodegradation of synthetic polymer was determined by testing the loss of gravimetric weight loss Results a) Biodegradation of gelatine b) The data in Table 3 shows that the major part of the gelatine was degraded by the bacteria after 1 week. Only trace amounts of protein could be detected after 2 weeks.

TABLE 3

| Residual protein (mg/ml) | | |
|---|---|---|
| | Incubation time (weeks) | |
| Treatment | 1 | 2 |
| Control | 0.25 | 0.27 |
| Isolate 5 | 0.06 | 0.05 |
| Isolate 6 | 0.06 | 0.03 |
| Soil consortium | 0.09 | 0.04 |

a) Biodegradation of synthetic polymer

The data in Table 4 shows that more than 20% of the polymer was degraded by the bacteria after incubation of 8 weeks.

Conclusions

1) Unspecified soil bacteria completely degrade the protein component of the polymer (i.e. gelatine)
2) These bacteria degraded the synthetic polymer since the weight content of the gelatine is 10% whereas the total weight loss of samples was 20-24%. This is considered to be a relatively high degradation rate since it was obtained in only 8 weeks
3) The data indicate that degradation can be performed by the general non-specific microbial populations without the need for enrichment cultures

TABLE 4

| Reduction in gravimetric weight (% of dry weight loss) | |
|---|---|
| Bacteria | Weight loss after 8 weeks |
| Isolate 5 | 24.1 ± 0.6 |
| Isolate 6 | 23.4 ± 3.8 |
| Soil consortium | 19.9 ± 3.3 |
| Control* | 236 mg |

*The dry weight of the non-inoculated medium served as the 100% value for calculating the % of weight loss

** Samples were evaporated in a boiling water bath and then dried in an oven at 105° C. until no change in weight was recorded.

Example 4

Figure 4A:
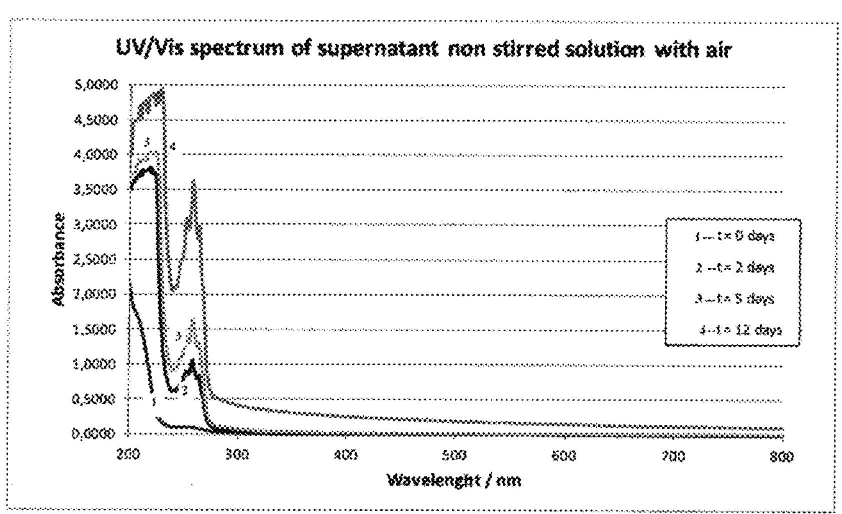
FIGS. 4A-4B. UV-VIS spectra for biodegradation of SMA-Na salt with *Pseudomonas* microbes using a method from Niall D. O'Leary et al (2002) (FIG. 4A) and biodegradation mechanism of SMA-Na salt (FIG. 4B).
Figure 4B:
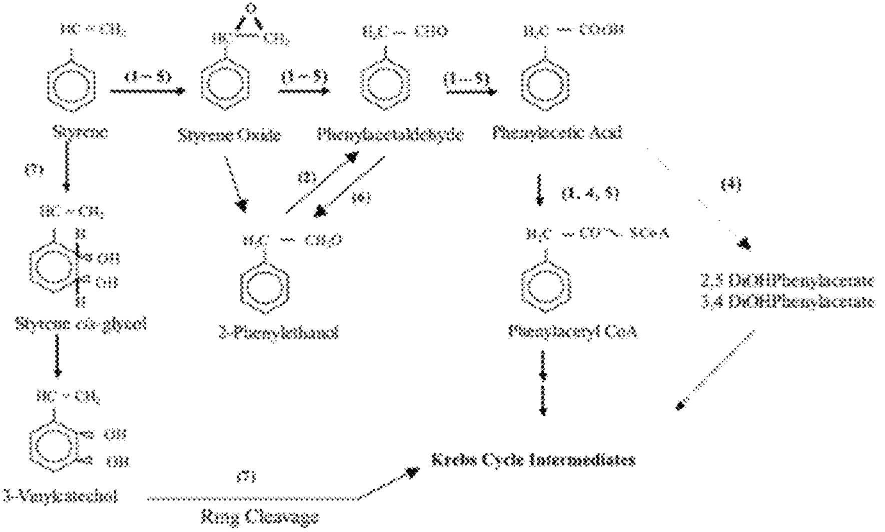

This example presents a test of biodegradation for SMA-sodium salt using *Pseudomonas* bacteria which is very abundant in the nature. There has been prepared a solution of SMA-sodium salt in which has been inoculated *Pseudomonas* bacteria using the experimental protocol from Niall D. O'Leary et al (2002). The solution has been maintained during 12 days without agitation in the presence of air and light to mimic an environmental phenomenon. It has been taken samples from this solution and studied in time by spectrophotometry UV-VIS. The results are presented in FIG. 4.*a*. It can be seen a band on UV zone below of 300 nm which is attributed to an aromatic ring as phenyl acetic acid. The intensity it goes up with the increase in time. The phenylacetic acid is not an aggressive substance to both the environment and humans. In FIG. 4.*b* is presented the scheme of the biodegradation mechanism.

Main Aspects

1. A process for the production of a superabsorbent polymer comprising:
a) synthesis of polymer (styrene-alt-maleic anhydride) copolymer by bulk polymerization method using excess of maleic anhydride as solvent in the presence of the polymerization inhibitors;
b) conversion of styrene-alt maleic anhydride copolymer to styrene-alt maleic acid copolymer by hydrolysis with water;
c) separation of styrene-alt-maleic acid copolymer from water suspension with free maleic acid by filtration when resulted supernatant as water solution of maleic acid and a filtrate as wet solid of styrene-alt maleic acid copolymer;
d) processing of maleic acid water solution for recovery of maleic anhydride by following operations:
concentration of maleic acid solution;
spray drying of concentrate maleic acid solution when is resulted maleic acid powder and water;
conversion of maleic acid powder to maleic anhydride by thermal vacuum dehydration.
e) preparation of monovalent cation hydroxide solution by dissolution of solid hydroxide in water;
f) preparation of styrene-alt maleic acid monovalent cation salt water solution by neutralization of styrene-maleic acid with monovalent cation solution;
g) preparation of biopolymer as water solution;
h) preparation of a binary composite polymer material by mixing of styrene-alt maleic acid monovalent cation salt solution with biopolymer water solution;
i) partial drying and granulation of the polymeric composite based on synthetic polymer and biopolymer;
j) supplementary drying of the granular polymeric composite partial dried
k) grinding of the granular mass dried in successive steps to obtain a large solid phase LSP and a small solid phase SSF, with the biggest particles less than 100 microns;
a) the big solid phase has particles' granulometry characteristic to SAP used for diaper;
b) the small solid phase SSF is re-used being added during the preparation of a new batch of SAP;
c) surface coating of LSP
d) thermal crosslinking of the coated LSP in two successive phase;
e) conditioning of LSP with bulk and surface crosslinked to obtain the end product SAP;
f) packaging of the end product in environmental conditions similarly with those used for conditioning.

2. A process for the production of a superabsorbent polymer as in 1 wherein the monomer of styrene is stabilized with organic compounds that inhibit the process of homopolymerization during storage and transportation, such as: amino derivatives, derived type of thiols, and hydroxyl derivate as example (2-hydroxypropyl)-ethylene diamine compounds, 4-tert-butylcatechol and others) being preferred 4-tert-butylcatechol in proportion of 0.002-0.008% to the monomer, more preferably is 0.003-0.007% to the styrene and most preferably 0.004-0.006% to the styrene.

3. A process for the production of a superabsorbent polymer as in aspects 1 and 2 wherein the molar fraction of styrene in the reaction mass is 0.05-0.08, preferably 0.1-0.15 and more preferably 0.18-0.21.

4. A process for the production of a superabsorbent polymer as in aspects 1-3 wherein the copolymerization of maleic anhydride with styrene are used thermic initiators as peroxides, azo compounds and other similar chemical agents, and the quantity of initiator is 0.05-0.15%, preferably 0.07-0.009% and most preferably 0.08-0.12% to a double quantity of styrene adopted for copolymerization.

5. A process for the production of a superabsorbent polymer as in aspects 1-4, wherein for the preparation of the copolymer of styrene and maleic anhydride is used the recovered maleic anhydride MAnh-R that resulted from a previous process of copolymerization (previous batch) and fresh maleic anhydride MAnh with a MAnh: MAnh-R ratio of 10-40% (dry basis) in correlation with the value adopted for the molar fraction of maleic anhydride used in the previous batch.

6. A process for the production of a superabsorbent polymer as in aspects 1-5 wherein conversion of styrene-alt maleic anhydride copolymer to styrene-alt maleic acid copolymer by hydrolysis using a quantity of water higher than the one stoichiometric required for total hydrolysis (Ws) with an excess which represents 2-3% versus to the stoichiometric value, preferably in excess of 4-5% to the stoichiometric water and most preferably 5-10% in excess to the stoichiometric water.

7. A process for the production of a superabsorbent polymer as in aspects 1-6 wherein total quantity of water necessary to styrene and maleic anhydride copolymer's hydrolysis is inserted in the mass of reaction in two steps from which 50% is in the form of 0.005 N hydrochloric acid solution and the rest as non-acidulated water.

8. A process for the production of a superabsorbent polymer as in aspects 1-7 wherein the acidulated water is inserted into the reaction mass in two portions at a temperature that not exceeds 60° C. at 15 minutes intervals between each dosage, and the quantity of non-acidulated water is inserted into the mass of reaction also in two portions, from which the first is after 60 minutes from the last portion of acidulated water, then is inserted the last serving of non-acidulated water and mixing of reaction mass for 45-60 minutes in cooling conditions of 35-40° C.

9. A process for the production of a superabsorbent polymer as in aspects 1-8 wherein the reaction mass obtained after copolymerization and hydrolysis is separated by filtration resulting a mix of styrene maleic acid copolymer (SMAC) and free maleic acid (MAC), which contain traces of non-reacted styrene and styrene stabilizer and traces of hydrochloric acid.

10. A process for the production of a superabsorbent polymer as in aspects 1-9 wherein the synthetic polymer SMAC is separated from the reaction mass by filtration as filtrate in solid form together with the supernatant as an aqueous solution which contain mostly maleic acid.

11. A process for the production of a superabsorbent polymer as in aspects 1-10 wherein the styrene maleic acid copolymer as wet solid resulted after separation from maleic acid by filtration is purified by:
- extraction of free maleic acid fraction from SMAC polymer mass which occurs by adding a quantity of deionized water [Wp] over the reaction mass;
- the quantity of water is correlated to the wet mass of reactions (RM) in accordance with the relationship $W_p=2*RM$, preferably $W_p=5*RM$, and most preferably $W_p=3*RM$;
- the extraction process occurs under mixing in a tank in 3-5 stages at temperature of 60° C. for 30 minutes followed each time by filtration using a Nuce or press filter;
- the number of extraction and filtration operations are established so that the content of the free carboxylic groups found in SMAC polymer to be between 0.00909-0.0095 mole/gram, preferably between 0.0091-0.0094 mole/gram and most preferably between 0.0092-0.0093 mole/gram;
- all solutions resulted from filtering are collected into a tank of supernatant in order to process the maleic acid which it contain.

12. A process for the production of a superabsorbent polymer as in aspects 1-11 wherein processing of maleic acid water solution to recovery of maleic anhydride consists from following operations:
- concentration of maleic acid solution through reverse osmosis;
- spray drying of concentrate maleic acid solution when results maleic acid powder and water;
- conversion of maleic acid powder to maleic anhydride by thermal-vacuum dehydration when in the end is obtained a material called recovered maleic anhydride (MAnh-R).

13. The recovered maleic anhydride (MAnh-R) as in aspect 12 is used in a new process of copolymerization with styrene by mixing with fresh maleic anhydride (MAnh).

14. A process for the production of a superabsorbent polymer as in aspects 1-13 wherein styrene maleic acid copolymer purified resulted after last filtration is converted to styrene-alt maleic acid monovalent cation salt water solution by neutralization with monovalent cation hydroxide solution to obtain a copolymer salt solution higher than 25%, preferably higher than 35% and most preferably higher than 50%.

15. A process for the production of a superabsorbent polymer as in aspects 1-14 wherein neutralization of SMAC copolymer is 48-58%, preferably 50-56% and most preferably 52-54%.

16. A process for the production of a superabsorbent polymer as in aspects 1-15 wherein is used a quantity of biopolymer that represents 4-6% (dry basis) to copolymer of styrene maleic acid, preferably 8-10% (dry basis) and most preferably 12-14% (dry basis).

17. A process for the production of a superabsorbent polymer as in aspects 1, 15 and 16 wherein the biopolymer is of animal or vegetal origin as: gelatin, albumin, casein, soy, guar or starch, preferably being gelatin.

18. A process for the production of a superabsorbent polymer as in aspects 1-17 wherein the preparation of polymeric composite is done by mixing of styrene maleic acid monocation salt with biopolymer solution at temperature of 55-75° C. for 30 minutes.

19. A process for the production of a superabsorbent polymer as in aspects 1-18 wherein is added small solid phase (SSF), resulted at the grinding of composite based on synthetic polymer and biopolymer from a previous batch, to the new solution of composite polymer.

20. A process for the production of a superabsorbent polymer as in aspects 1-19 wherein the blend of polymeric composite soluble in water which contain also the small solid phase is concentrated by mixing under vacuum of 10-20 mbar at temperature of 65° C. for 4-5 hours until the viscous solution is transformed in a granular mass with a humidity not higher than 20%.

21. A process for the production of a superabsorbent polymer as in aspects 1-20 wherein the granular polymeric mass is supplementary dried in preheat air at temperature of 75-85° C. in order to final drying of polymeric composite until the moisture content is less than 14%, preferably a drying to a moisture content less than 12% and most preferably to a moisture content of less than 8%.

22. A process for the production of a superabsorbent polymer as in aspects 1-21 where the dried water soluble polymer composite is grinded and sieved in several stages so as to obtain two kinds of solid phases: large solid phase LSP) and small solid phase (SSF).

23. A process for the production of a superabsorbent polymer as in aspects 1-22 wherein the solid phase LSP is subdue to a a coating process using known chemical substances such as: glycerin ethylene glycol, propylene glycol or polyether hydroxyl with properties of biodegradability, preferably hydroxyl polyether and the most preferably is polyethylene glycol-PEG 200 used at a rate of 0.2-2% by weight (dry basis) to LSP, preferably at a rate of 0.5-1.5% by weight and most preferably at a rate of 0.8-1.2% by weight to LSP.

24. A process for the production of a superabsorbent polymer as in aspects 1-23 wherein the surface coating is made in powder coating machines type at temperature of 30-70° C., preferably at temperatures of 35-65° C. and most preferably at temperatures of 40-60° C. for 30-90 minutes, preferably for 40-75 minutes and most preferably for 50-60 minutes, resulting the material called Polymer Composite Coated Treated (PCC).

25. A process for the production of a superabsorbent polymer as in aspects 1-24 wherein the obtained material after surface coating (Polymer Composite Coated) is subdue to a thermal treatment called first thermal treatment (TT1) consisting in warming of particles mass in hot air with temperature of 90-140° C. for 30-150 minutes, preferably with temperatures of 100-135° C. for 45-120 minutes and most preferably by bulk thermal crosslinking at temperatures of 110-120° C., for 60-90 minute, using conveyor belt type or shaking rotary type; to obtain an intermediary material called Polymer Composite Coated first cross linked (PCC-CL-1).

26. A process for the production of a superabsorbent polymer as in aspects 1-25 wherein the material PCC-CL-1 is subdue to a new thermal treatment (TT2) in hot air with temperature of 120-150° C. for 5-30 minutes, preferably at temperatures of 125-145° C. for 10-25 minutes and most preferably to temperature of 120-140° C. for 15-20 minute in the same type of equipment used for TT1 and is obtained the Polymer Composite Coated second cross linked (PCC-CL-2).

27. A process for the production of a superabsorbent polymer as in aspects 1-26 wherein the material (PCC-CL-2) is conditioned for 24 hours in an atmosphere of air with a moisture content of 65% and temperature of 20° C. and then is packed in scaled polyethylene bags.

28. A process for the production of a superabsorbent polymer as in aspects 1-27 wherein the material is a biodegradable SAP with AUL higher than 20 g/g in aqueous solution of 0.9% NaCl at pressure of 0.9 psi.

REFERENCES

1. Allan S. Hoffman "Hydrogels for biomedical applications"—Advanced Drug Delivery Reviews 43 (2002) 3-12
2. Enas M. Ahmed Hydrogel: Preparation, characterization and applications: A review, Journal of Advanced Research Volume 6, Issue 2, March 2015, Pages 105-121
3. Mohammad J. Zohuriaan-Mehr and Kourosh Kabiri "Superabsorbent Polymer Materials A Review"—Iranian Polymer Journal 17 (6), 2008, 451-477
4. Rajiv Dabhi, Neelkanth Bhatt and Bipin Pandit "Superabsorbent Polymer Materials—an Innovative water saving technique for optimization of crop yield"—Vol. 2, Issue 10, October 2013-533-5340
5. Fidelio N. Nnadi, Super Absorbent Polymer (SAP) and Irrigation Water Conservation, Irrigation & Drainage Systems Engineering, Irrigation Drainage Sys Eng 1:1, 2012
6. Suda Kiatkamjornwong "Superabsorbent Polymers and Superabsorbent Polymer Composites"—Science Asia 33 Supplement 1 (2007): 39-43
7. Fidelia Nnadi and Chris Brave "Environmentally friendly superabsorbent polymers for water conservation in agricultural lands"—Journal of Soil Science and Environmental Management Vol. 2 (7), pp. 206-211, July 2011
8. Giuseppe Cannazza, Andrea Cataldo, Egidio De Benedetto, Christian Demitri, Marta Madaghiele and Alessandro Sannino "Experimental Assessment of the Use of a Novel Superabsorbent polymer (SAP) for the Optimization of Water Consumption in Agricultural Irrigation Process"—Water 2014, 6, 2056-2069
9. C. Demitri, F. Scalera, M. Madaghiele, A. Sannino, and A. Maffezzoli "Potential of Cellulose-Based Superabsorbent Hydrogels as Water Reservoir in Agriculture"—International Journal of Polymer Science Volume 2013, Article ID 435073, 6 pages
10. Mohammad Sadeghi and Fatemeh Soleimani "Synthesis and Characterization of Superabsorbent Hydrogels for Oral Drug Delivery Systems" International Journal of Chemical Engineering and Applications, Vol. 2, No. 5, October 2011
11. Deniz Aydemir, Alper Kiziltas, Gokhan Gunduz "Natural Fillers-filled Styrene-Maleic Anhydride Copolymer Composites"—Wood Research—60 (1): 2015, 167-174
12. Sahibi Belkhiria, Thhierry Mieyer, Albert Renken "Styrene Maleic Anhydride Copolymerization in a Recycle Tubular Reactor; Reactor stability and Product Quality"—Chemical Engineering Science. Vol. 49, No. 248, pp. 4981-4990. (1994)
13. Raphael M. Ottenbrite, Samuel J. Huang, Kinam Park "Hydrogels and Biodegradable Polymers for Bioapplications"—ACS Symposium Series 627—the 208th National Meeting of the American Chemical Society, Washington, DC Aug. 21-26, 1994
14. Andreas Lendlein and Adam Sisson "Handbook of Biodegradable Polymers-Synthesis, Characterization and Applications"—2011 Wiley-VCH Verlag & Co. KGaA Boschstr. 12, 69469 Weinheim, Germany
15. Abraham J. Domb, Joseph Kost, David M. Wiseman "Hand Book of Biodegradable Polymers" Published in 1997 by CRC Press ISBN 10: 90-5702-153-6
16. Steffen Jockusch, Nicholas J. Turro, Yoshiro Mitsukami, Makoto Matsumoto—"Photoinduced Surface Crosslinking of Superabsorbent Polymer Particles"—J Appl Polym Sci 111: 2163-2170, (2009)
17. Hossein Hosseinzadeh "Synthesis and swelling properties of a poly(vinyl alcohol)-based superabsorbing hydrogel"—Current Chemistry Letters 2 (2013) 153-158
18. D. M. G. Comissiong. L. K. Gross. V. A. Volpert "The enhancement of weakly exothermic polymerization fronts"—J Eng Math (2007) 57: 423-435
19. Inderjeet Kaur, Vandna Kumari and Bikram Singh "Synthesis and Characterization of Acrylic acid Grafted Styrene-Maleic anhydride Copolymer"—Der Chemica Sinica, 2012, 3 (2): 343-358
20. K. V. Middle, R. Bussey, L. Cusco, D. Kerr, T. J. Snee "Reaction inhibition in the control of exothermic runaway in "Safety and Security Engineering"—WIT Transactions on The Built Environment, Vol 82, 2005 WIT Press
21. Roman Geier, Christina Wappl, Hilde Freiszmuth, Christian Slugove and Georg Gescheidt "Thermal effects in polymerisations—a live view differentiating between bulk effects, thermal diffusion, and oxygen inhibition"—| Polym. Chem., 2015, 6, 2488-2492
22. Nedal Y. Abu-Thabit "Thermochemistry of Acrylamide Polymerization: An Illustration of Auto-acceleration and Gel Effect"—World Journal of Chemical Education, 2017, Vol. 5, No. 3, 94-101
23. S. M. Rowe "Polymerization Reaction Inhibition an Alternative Basis of Safety"—ICHEME SYMPOSIUM SERIES NO. 141 (1997)
24. Deniz Aydemir et. al. (2015) "Natural Fillers-Filled Styrene Maleic Anhydride Copolymer Composites"—WOOD RESEARCH: 60 (1): 2015: 167-174
25. Zakir M. O. Rzayev (2011) "Graft Copolymers of Maleic Anhydride and Its Isostructural Analogues High Performance Engineering Materials" Int. Rev. Chem. Eng., 3 (2011) 153-215
26. Inderjeet Kaur et al. (2012) "Synthesis and Characterization of Acrylic acid Grafted Styrene-Maleic anhydride Copolymer"—Der Chemica Sinica, 2012, 3 (2): 343-358
27. A. S. Almeid et al. (2008) "Simulation of styrene polymerization reactors: kinetic and thermodynamic modeling" Brazilian Journal of Chemical Engineering—Vol. 25, No. 02, pp. 337-349, April-June 2008
28. D. M. G. Comissiong et al. (2007) "The enhancement of weakly exothermic polymerization fronts"—J Eng Math (2007) 57: 423-435
29. Z. Florjanczyk et al. (2000) "Lithium gel polyelectrolytes based on crosslinked maleic anhydride-styrene copolymer" Electrochimica Acta 45 (2000) 3563-3571
30. Zbigniew Florjanczyk et al. (1998) "Highly Conducting Lithium Polyelectrolytes Based on Maleic Anhydride-Styrene Copolymers"—J. Phys. Chem. B 1998, 102, 8409-8416
31. Ankush B. Argade et al. (1998) "Poly(acrylic acid)-Poly(vinyl alcohol) Copolymers with Superabsorbent Properties"—J Appl Polym Sci 70: 817-829, 1998
32. Francesco F. Montesano et al. (2015) "Biodegradable Superabsorbent Hydrogel Increases Water Retention Properties of Growing Media and Plant Growth"—Agriculture and Agricultural Science Procedia 4 (2015) 451-458
33. Fidelia Nnadi et al (2011). "Environmentally friendly superabsorbent polymers for water conservation in agricultural lands'—Journal of Soil Science and Environmental Management Vol. 2 (7), pp. 206-211, July 2011
35. Alessandro Sannino et al (2009) "Biodegradable Cellulose-based Hydrogels: Design and Applications"—Materials 2009, 2, 353-373
36. Rakesh Singh et al (2013)." "Biodegradation of Styrene-Butadiene-Styrene Copolymer via Sugars Attached to the Polymer Chain" Advances in Materials Physics and Chemistry, 2013, 3, 112-118
37. P. Galgali et al (2004) "Fungal degradation of carbohydrate-linked polystyrenes"—Carbohydrate Polymers 55 (2004) 393-399.
38. Niall D. O'Leary et al (2002) "Biochemistry, genetics and physiology of microbial styrene degradation" FEMS Microbiology Reviews 26 (2002) 403-417
39. Fredric L. Buchholz Andrew T. Graham (1998) "MODERN SUPERABSORBENT POLYMER TECHNOLOGY"—WILEY-VC New York I Chichester I Weinheim I Brisbane I Singapore I Toronto 1998

| Pat. No. | Date | Inventor |
|---|---|---|
| U.S. Pat. No. 2,479,522 | 16 Aug. 1949 | Strain |
| U.S. Pat. No. 2,640,819 | 2 Jun. 1953 | Barrett Gerald R |
| U.S. Pat. No. 2,855,387 | 7 Oct. 1958 | Barrett Gerald R |
| U.S. Pat. No. 2,996,480 | 15 Aug. 1961 | Mulloy et, al. |
| U.S. Pat. No. 3,933,747 | Jan. 20, 1976 | Nowak, et al. |
| U.S. Pat. No. 3,954,721 | May 4, 1976 | Gross |
| U.S. Pat. No. 3,959,569 | May 25, 1976 | Burkholder, Jr. |
| U.S. Pat. No. 3,980,663 | Sep. 14, 1976 | Gross |
| U.S. Pat. No. 3,983,095 | Sep. 28, 1976 | Bashaw, et al. |
| U.S. Pat. No. 3,983,271 | 28 Sep. 76 | Pangle, Jr., et al. |
| U.S. Pat. No. 3,989,586 | 2 Nov. 76 | Bashaw, et al. |
| U.S. Pat. No. 4,034,014 | 5 Jul. 1977 | Curtis, Jr., et al. |
| U.S. Pat. No. 4,041,228 | 9 Aug. 1977 | Gross |
| U.S. Pat. No. 4,051,311 | 27 Sep. 1977 | Lee |
| U.S. Pat. No. 4,076,673 | 28 Feb. 1978 | Burkholder, Jr. |
| U.S. Pat. No. 4,076,917 | 28 Feb. 1978 | Swift, et al. |
| U.S. Pat. No. 4,101,606 | Jul. 18, 1978 | Cenci, et al. |
| U.S. Pat. No. 4,117,184 | 26 Sep. 1978 | Erickson, et al. |
| U.S. Pat. No. 4,154,646 | 15 May 1979 | Rave |
| U.S. Pat. No. 4,167,464 | 11 Sep. 1979 | George |
| U.S. Pat. No. 4,251,643 | 17 Feb. 1981 | Harada, et al. |
| U.S. Pat. No. 4,389,513 | 21 Jun. 1983 | Miyazaki |
| U.S. Pat. No. 4,390,672 | Jun. 28, 1983 | von Bonin |
| U.S. Pat. No. 4,418,163 | 29 Nov. 1983 | Murakami, et al. |
| U.S. Pat. No. 4,468,343 | Aug. 28, 1984 | Butler, et al. |
| U.S. Pat. No. 4,500,670 | 19 Feb. 1985 | McKinley, et al. |
| U.S. Pat. No. 4,666,983 | 19 May 1987 | Tsubakimoto, et al. |
| U.S. Pat. No. 4,734,478 | 29 Mar. 1988 | Tsubakimoto, et al. |
| U.S. Pat. No. 4,758,617 | 19 Jul. 1988 | Tanioku, et al. |
| U.S. Pat. No. 4,771,105 | 13 Sep. 1988 | Shirai, et al. |
| U.S. Pat. No. 4,820,773 | Apr. 11, 1989 | Alexander, et al. |
| U.S. Pat. No. 4,824,901 | Apr. 25, 1989 | Alexander, et al. |
| U.S. Pat. No. 4,855,179 | 8 Aug. 1989 | Bourland, et al. |
| U.S. Pat. No. 4,888,238 | 19 Dec. 1989 | Katz, et al. |
| U.S. Pat. No. 4,950,692 | 21 Aug. 1990 | Lewis, et al. |
| U.S. Pat. No. 4,954,562 | 4 Sep. 1990 | Anderson |
| U.S. Pat. No. 4,963,638 | 16 Oct. 1990 | Pazos, et al. |
| U.S. Pat. No. 5,002,986 | 26 Mar. 1991 | Fujiura, et al. |
| U.S. Pat. No. 5,026,784 | Jun. 25, 1991 | Le-Khac |
| U.S. Pat. No. 5,221,787 | 22 Jun. 1993 | Robison, et al. |
| U.S. Pat. No. 5,385,729 | 31 Jan. 1995 | Prencipe, et al. |
| U.S. Pat. No. 5,466,731 | 14 Nov. 1995 | Akers, et al. |
| U.S. Pat. No. 5,693,707 | 2 Dec. 1997 | Cheng, et al. |
| U.S. Pat. No. 5,703,186 | 30 Dec. 1997 | Sezi, et al. |
| U.S. Pat. No. 5,733,994 | 31 Mar. 1998 | Koepff, et al. |
| U.S. Pat. No. 5,846,214 | 8 Dec. 1998 | Makuuchi, et al. |
| U.S. Pat. No. 5,847,089 | 8 Dec. 1998 | Damodaran, et al. |
| U.S. Pat. No. 6,087,448 | 11 Jul. 2000 | Mitchell, et al. |
| U.S. Pat. No. 6,689,378 | 10 Feb. 2004 | Sun, et al. |
| U.S. Pat. No. 7,166,356 | 23 Jan. 2007 | Flohr |
| U.S. Pat. No. 7,985,819 | 26 Jul. 2011 | Bucevschi, et al. |
| U.S. Pat. No. 8,013,083 | 6 Sep. 2011 | Kosover, et al. |
| U.S. Pat. No. 8,022,140 | 20 Sep. 2011 | Tikart, et al. |
| US20100139347 | 10 Jun. 2010 | Barati et, al. |
| EP1833521 | 5 Aug. 2009 | Azad et, al. |
| EP2277557 | 25 Jun. 2014 | Lindner et, al. |
| US20080200616 | Aug. 21, 2008 | Tanizaki,et al. |
| US20080227944 | Sep. 18, 2008 | Ambrosio, et al. |
| US20090324537 | Dec. 31, 2009 | Bucevschi, et al. |
| US20100234233 | 16 Sep. 2010 | Ambrosio, et al. |

The invention claimed is:

1. A biodegradable polymeric composite-forming composition, comprising:

a styrene maleic acid copolymer (SMAC) in acid form and/or anionic form;

a counterion when SMAC is in anionic form, said counterion, when present being $Li^{(+)}$, $Na^{(+)}$, $K^{(+)}$, or $NH_4^{(+)}$;

a biopolymer; and a crosslinking agent selected from the group consisting of glycerin, ethylene glycol, propylene glycol, polyethylene glycol and polyether hydroxyl.

2. The composite-forming composition of claim 1, wherein the amount of biopolymer relative to SMAC in the composition is at least 4-6% (dry basis).

3. The composite-forming composition of claim 2, wherein the amount of biopolymer relative to SMAC in the composition is at least 8-10% (dry basis).

4. The composite-forming composition of claim 3, wherein the amount of biopolymer relative to SMAC in the composition is at least 12-14% (dry basis).

5. A process for the production of a superabsorbent biodegradable polymeric composite, comprising:

(a) synthesize styrene-alt-maleic anhydride copolymer by bulk polymerization method using excess of maleic anhydride as solvent in the presence of polymerization initiators;

(b) convert the styrene-alt maleic anhydride copolymer to styrene-alt maleic acid copolymer (SMAC) by hydrolysis with water;

(c) separate SMAC from water suspension by filtration;

(d) neutralize the SMAC of (c) with a base solution to obtain a water solution of poly(styrene-alt maleic acid) sodium salt;

(e) mix the styrene-alt maleic acid copolymer salt solution of (d) with a biopolymer water solution to obtain a binary composite polymer material;

(f) dry and grind the material obtained in (e) to obtain a large solid phase (LSP) with particle size of at least 100 microns and a small solid phase (SSF) with the remainder of the particle sizes;

(g) surface coat the LSP with a compound selected from the group consisting of glycerin, ethylene glycol, propylene glycol, polyethylene glycol and polyether hydroxyl; and (h) thermally crosslink the coated LSP to obtain biodegradable composite polymer.

6. The process of claim 5, where the LSP has particle size of at least 150 microns.

7. The process of claim 5, wherein the LSP has granulometric distribution higher than 100 microns.

8. The process of claim 5, wherein the SSF has granulometric distribution up to 100 microns.

9. In a diaper containing a biodegradable polymeric composite, the improvement wherein the biodegradable polymeric composite is the biodegradable polymeric composite produced by the process of claim 5.

10. A process of preparing a biodegradable polymeric composite, comprising:

(a) mixing an aqueous solution of a synthetic copolymer of styrene-maleic acid with an aqueous solution of an inorganic base to form polymer-inorganic salt;

(b) adding an aqueous solution of a biopolymer to the polymer-inorganic salt of step (a) to form an aqueous polymeric mixture;

(c) drying and grinding the polymeric mixture obtained in (b) to obtain at least one solid phase polymeric material characterized by particle size of 100 microns and higher;

(d) coating the polymeric material of (c) with a compound selected from the group consisting of glycerin, ethylene glycol, propylene glycol, polyethylene glycol and polyether hydroxyl; and e) thermally crosslinking the polymeric material of step (d) to form biodegradable composite polymer.

11. The process of claim 7, wherein the LSP has granulometric distribution of 100-850 microns.

* * * * *